(12) United States Patent
Knaup et al.

(10) Patent No.: US 11,219,235 B2
(45) Date of Patent: Jan. 11, 2022

(54) METHOD FOR PREPARING A COMPOSITION COMPRISING OMEGA-3 FATTY ACID SALTS AND AMINES

(71) Applicant: Evonik Operations GmbH, Essen (DE)

(72) Inventors: Guenter Knaup, Bruchkoebel (DE); Milan Latinovic, Nidda (DE); Joerg Lotz, Kalbach (DE); Michael Schwarm, Alzenau (DE)

(73) Assignee: Evonik Operations GmbH, Essen (DE)

( * ) Notice: Subject to any disclaimer, the term of this patent is extended or adjusted under 35 U.S.C. 154(b) by 109 days.

(21) Appl. No.: 16/304,227

(22) PCT Filed: May 24, 2017

(86) PCT No.: PCT/EP2017/062582
§ 371 (c)(1),
(2) Date: Nov. 23, 2018

(87) PCT Pub. No.: WO2017/202935
PCT Pub. Date: Nov. 30, 2017

(65) Prior Publication Data
US 2020/0315230 A1    Oct. 8, 2020

(30) Foreign Application Priority Data
May 25, 2016 (EP) ..................... 16171275

(51) Int. Cl.
| | | |
|---|---|---|
| *A23P 30/20* | (2016.01) | |
| *A23L 33/12* | (2016.01) | |
| *A23L 33/175* | (2016.01) | |
| *A23D 7/005* | (2006.01) | |
| *A61K 31/202* | (2006.01) | |

(52) U.S. Cl.
CPC ............ *A23L 33/12* (2016.08); *A23D 7/0053* (2013.01); *A23L 33/175* (2016.08); *A23P 30/20* (2016.08); *A61K 31/202* (2013.01)

(58) Field of Classification Search
CPC ..... A23L 33/12; A23L 33/175; A23D 7/0053; A23P 30/20; A61K 31/202; A61K 31/198; A61K 2300/00
See application file for complete search history.

(56) References Cited

U.S. PATENT DOCUMENTS

| 5,750,572 A | 5/1998 | Bruzzese |
|---|---|---|
| 2008/0131519 A1 | 6/2008 | Szilbereky et al. |
| 2016/0199385 A1 | 7/2016 | Sciavolino et al. |

FOREIGN PATENT DOCUMENTS

| EP | 0 734 373 B1 * | 4/1998 |
|---|---|---|
| GB | 2 216 418 A | 10/1989 |
| GB | 2 216 522 A | 10/1989 |
| KR | 2003-0053484 A | 6/2003 |
| WO | WO 95/16661 A1 | 6/1995 |
| WO | WO 2006/059169 A2 | 6/2006 |
| WO | WO 2015/195491 A1 | 12/2015 |
| WO | WO 2016/049018 A1 | 3/2016 |

OTHER PUBLICATIONS

Vural Gökmen, et al; title: Development of functional bread containing nanoencapsulated omega-3 fatty acids; Journal of Food Engineering, vol. 105; pp. 585-591; online Mar. 21, 2011. (Year: 2011).*
Nih (titled Omega-3 Fatty Acids Fact Sheet for Consumers, downloaded from ttps://ods.od.nih.gov/factsheets/Omega3FattyAcids-Consumer/?print=1 on Oct. 14, 2020. (Year: 2020).*
Geleijnse, et al, title: reduction in blood pressure with a low sodium, high potassium, and high magnesium salt in older subjects with mild to moderate hypertension; BMJ vol. 309; pp. 436-440; Aug. 13, 1994. (Year: 1994).*
Shahidi et al; title: Lipid oxidation and improving the oxidative stability; Chem. Soc. Rev., 2010, 39, 4067-4079. (Year: 2010).*
U.S. Appl. No. 15/538,719, filed Jun. 22, 2017, US 2017-0367394 A1, Guenter Knaup, et al.
U.S. Appl. No. 15/538,825, filed Jun. 22, 2017, US 2017-0360072 A1, Guenter Knaup, et al.
U.S. Appl. No. 16/304,178, filed Nov. 23, 2018, Thomas Gottstein, et al.
U.S. Appl. No. 16/304,227, filed Nov. 23, 2018, Guenter Knaup, et al.
International Search Report and Written Opinion dated Jul. 13, 2017 in PCT/EP2017/062582, citing documents AA-AC, AN-AS, and AV-AY therein, 14 pages.
"Water-soluble lipid composite containing basic amino acid and preparation method thereof" DERWENT, XP002389259, 2003, 1 page.
Novales, B. et al. "Self-Assembly and Foaming Properties of Fatty Acid-Lysine Aqueous Dispersions" Langmuir, vol. 26, No. 8, XP009190778, 2010, pp. 5329-5334.
Kim, Y.J. et al. "Total Antioxidant Capacity of Arginine-Conjugated Linoleic Acid (CLA) Complex" Journal of Agricultural and Food Chemistry, vol. 52, No. 3, XP055172184, 2004, pp. 439-444.

* cited by examiner

*Primary Examiner* — Yanzhi Zhang
(74) *Attorney, Agent, or Firm* — Oblon, McClelland, Maier & Neustadt, L.L.P.

(57) ABSTRACT

The present invention relates to a method for preparing a composition comprising one or more omega-3 fatty acid salt(s), the composition obtainable or obtained by this method, and also the use of this composition for the preparation of foodstuffs, food supplements or pharmaceutical products.

16 Claims, No Drawings

METHOD FOR PREPARING A COMPOSITION COMPRISING OMEGA-3 FATTY ACID SALTS AND AMINES

Due to an extensive collection of scientific evidence compiled over recent decades, numerous health advantages have been linked to the supplementary intake of polyunsaturated fatty acids (PUFAs). The prevention of cardiovascular disease and the reduction of symptoms of inflammation are among the most important examples, and also, inter alia, the prevention of the promotion and progression phase of some types of cancer, the lowering of blood pressure and cholesterol level and also positive effects in the treatment of depression and schizophrenia, Alzheimer's, dyslexia, attention deficit disorder and hyperactivity have been reported. Since it is believed that some PUFAs are essential for the development of the brain, nervous system and the eyes, it is also nowadays routine to enrich infant formula with certain PUFAs.

The preparation of foodstuffs, food supplements and pharmaceutical products with PUFAs is however made difficult due to their sensitivity to oxidation. The oxidation of PUFAs has negative nutritional physiological and organoleptic consequences, such as alterations of the nutrient content by decomposition of important fatty acids; rancidity, which generates the flavour taints and pronounced odours; colour changes such as darkening of fats and oils; and also loss of flavour. The oxidative degradation of PUFAs generates a complex mixture of volatile secondary oxidation products and these generate in particular unpleasant flavour taints.

In the context of the present invention, the terms "PUFA" and "polyunsaturated fatty acid", are used synonymously and are as defined below: Fatty acids are classified according to the length and saturation of their carbon chain. Short chain fatty acids have 2 to about 6 carbon atoms and are typically saturated or unsaturated. Medium chain fatty acids have from about 6 to about 14 carbon atoms and are also typically saturated or unsaturated. Long chain fatty acids have from about 16 to 24 or more carbon atoms and may be saturated or unsaturated. Long chain fatty acids may have one or more unsaturated sites which leads to the terms "monounsaturated" or "polyunsaturated". In the context of the present invention, long chain polyunsaturated fatty acids having 18 or more carbon atoms are referred to as "polyunsaturated fatty acids" or "PUFAs".

According to standard nomenclature, PUFAs are classified according to the number and position of the double bonds. There are several series or families of PUFAs, depending on the position of the double bond which is closest to the methyl end of the fatty acid. There are two series of particular nutritional physiological meaning: the omega-3 series comprises one double bond at the third carbon atom, while the omega-6 series has no double bonds up to the sixth carbon atom. Thus, docosahexaenoic acid ("DHA") has a chain length of 22 carbon atoms with 6 double bonds beginning with the third carbon atom from the methyl end and is referred to as "22:6 n-3" (all-cis-4,7,10,13,16,19-docosahexaenoic acid). Another important omega-3 fatty acid is eicosapentaenoic acid ("EPA"), which is referred to as "20:5 n-3" (all-cis-5,8,11,14,17-eicosapentaenoic acid). An important omega-6 fatty acid is arachidonic acid ("ARA"), which is referred to as "20:4 n-6" (all-cis-5,8,11,14-eicosatetraenoic acid).

Salts of polyunsaturated omega-3 fatty acids with basic amino acids are known, such as are described in EP 0734373 B1. L-lysine salts of omega-3 fatty acids have proven to be stable to oxidation compared to the free omega-3 fatty acids and the alkali metal and alkaline earth metal salts of omega-3 fatty acids. Alkali metal and alkaline earth metal salts of omega-3 fatty acids, and also the preparation thereof are described, for example, in EP 1 260 496 A1.

L-lysine salts of omega-3 fatty acids are thus prepared hitherto by reacting the free omega-3 fatty acids with L-lysine in a polar solvent or solvent mixture and the resulting mixtures are evaporated to dryness. Water or water-alcohol mixtures are used as solvent or solvent mixture. The omega-3 fatty acid L-lysine salts are either obtained as solids with waxy consistency, described for instance in EP 0734373 B1, or as crystalline substances with melting points with decomposition of ca. 190° C., described for instance in DE 39 07 649 C2.

The evaporation of solutions of omega-3 fatty acid L-lysine salts in water or water-alcohol mixtures under reduced pressure is a very energy-intensive process. Moreover, the process is technically very difficult to accomplish, since the omega-3 fatty acid L-lysine salts have surfactant properties and solutions thereof tend to foam when evaporated: on evaporation, the viscosity of the solutions increases markedly, until viscous gels are formed, which on further drying form solid foams.

A further possibility for isolating the omega-3 fatty acid L-lysine salts consists of spray-drying aqueous-ethanolic solutions at concentrations of omega-3 fatty acid L-lysine salts of >50% by weight. However, the use of an organic solvent in the spray-drying requires particular safety measures, an inert gas atmosphere for example. The costs are also significantly increased by the condensation of the solvent required.

There continues to be a need therefore for the most simple and effective method for preparing omega-3 fatty acid salts, which may be carried out both energy and cost-efficiently and using standard apparatuses without particular safety measures, and which afford the omega-3 fatty acid salts at the purity required for use as food additives.

It has now been found, surprisingly that omega-3 fatty acid salts may be obtained simply in that a paste comprising one or more omega-3 fatty acid(s), one or more basic amine(s) and 20% by weight or less water, based on the total weight of the paste, is kneaded at a temperature of 130° C. or less.

Accordingly, the present invention relates in a first aspect to a method for preparing a composition comprising one or more omega-3 fatty acid salt(s), characterized in that a paste comprising one or more omega-3 fatty acid(s), one or more basic amine(s) and 20% by weight or less water, based on the total weight of the paste, at a temperature of 130° C. or less is kneaded for a period of time between 30 seconds and 60 minutes until a homogenous paste is obtained.

In the context of the present invention, water of crystallization possibly present in the basic amine is considered in the calculation of the water content.

In the context of the present invention, the term "paste" is to be understood as a suspension that behaves as a solid until a sufficiently large load or stress is applied, at which point it flows like a fluid. The paste consists of a suspension of granular material in a background fluid (water). In the claimed process the paste is a dough-like material, meaning a thick, malleable and elastic paste. Within the claimed process, the paste can be kneaded and handled like a conventional dough.

The paste is obtained by mixing the omega-3 fatty acids with the basic amines in water (up to 20% by weight) for a period of time between 30 seconds and 60 minutes. The paste is considered homogenous, when the granular material and the oily phase in the background fluid is evenly distributed. The paste can then be compared with a conventional dough.

In the context of the present invention, the term "knead" is understood to agree with the definition in "Dictionary", that the dispersion is "worked into a uniform mixture by pressing".

In the simplest case, in the laboratory facility for example, the dispersion may be kneaded by using a mixer. In industrial applications, the kneading of the dispersion may be accomplished, for example, by means of an extruder. Therefore, it is also possible to carry out the method described here according to the invention continuously.

The degree of conversion of the reaction can in this case be determined quantitatively by means of IR spectroscopy, specifically by the shift of the C=O absorption band from about 1707 cm$^{-1}$ for free omega-3 fatty acid(s) to about 1578 cm$^{-1}$ after salt formation. A conversion of 90% by weight or more of the omega-3 fatty acid(s) to omega-3 fatty acid salt(s) therefore corresponds to a reduction of the C=O absorption band at about 1707 cm$^{-1}$ for free omega-3 fatty acid(s) to 10% or less. Suitable software which enables the quantitative evaluation of IR spectra is, for example, the program Opus Version 7.5 from Bruker Optics.

The time required in each case to have converted 90% by weight or more of the omega-3 fatty acid(s) to omega-3 fatty acid salt(s) is reciprocally related with the amount of water used and with the temperature set. According to the present invention, the time required to have converted 90% by weight or more of the omega-3 fatty acids to omega-3 fatty acid salts is between 30 sec and 60 min, preferably between 1 min and 30 min.

As has been mentioned at the outset, omega-3 fatty acids are sensitive to oxidation and temperature. As a measure of the oxidative decomposition, the anisidine number (AN) and peroxide number (PN) are typically determined. For thermal decomposition, the oligomer content which can be determined by gel chromatography is a suitable measure.

The peroxide number (PN) is a measure of primary oxidation products (hydroperoxide formation of double bonds), and the anisidine number (AN) is a measure of secondary decomposition products (carbonyl compounds). The TOTOX number is calculated as TOTOX=2*PN+AN (where PN is stated in milliequivalents of $O_2$ per kg of the sample). Methods for determining peroxide number (PN) and anisidine number (AN) are described in the literature, cf. e.g. "Official Methods and Recommended Practices of the AOCS", 6th edition 2013, published by David Firestone, ISBN 978-1-893997-74-5. PN may also be determined according to Ph. Eur. 2.5.5 (01/2008:20505), and AN may also be determined according to Ph. Eur. 2.5.36 (0172008:20536).

An example of a method for determining the peroxide number (PN) of a sample is carried out as follows:
Reagents and Solution:
1. Acetic acid-chloroform solution (7.2 ml of acetic acid and 4.8 ml of chloroform).
2. Saturated potassium iodide solution. Store protected from light.
3. Sodium thiosulphate solution, 0.1N. Obtainable commercially.
4. 1% starch solution. Obtainable commercially.
5. Distilled or deionized water.

Method:
Carry out a blank value determination of the reagents.
1. Weigh out 2.00 (±0.02) g of the sample in a 100 ml Erlenmeyer flask with ground glass stopper. Determine the weight to a precision of 0.01 g.
2. Add 12 ml of the acetic acid-chloroform solution using the measuring cylinder.
3. Swirl the Erlenmeyer flask until the sample is completely dissolved (careful heating on a hot plate is potentially required).
4. Add 0.2 ml of saturated potassium iodide solution with a measuring pipette.
5. Seal the Erlenmeyer flask with the stopper and swirl the content of the flask for exactly one minute.
6. Immediately add 12 ml of distilled or deionized water from the measuring cylinder, seal the flask with the stopper and shake vigorously in order to separate the iodine from the chloroform layer.
7. Fill 0.1N sodium thiosulphate in a burette.
8. If the starting colour of the solution is deep red-orange, titrate slowly with mixing until the colour is lighter. If the solution is light amber coloured at the start, go to step 9.
9. Using a metering device, add 1 ml of starch solution as indicator.
10. Titrate until the blue-grey colour in the aqueous phase (upper layer) disappears.
11. Record the exact ml value of the titrant to two decimal places.

Calculation:
S=Titration of the sample
B=Blank titration $$\text{Peroxide number} = (S-B)*N \text{ thiosulphate} * 1000/\text{sample weight}$$

An example of a method for determining the anisidine number (AN) of a sample is carried out as follows:

The anisidine number is defined as the 100-fold optical density measured in a 1 cm cell of a solution comprising 1 g of the substance to be investigated in 100 ml of a mixture of solvent and reagents according to the following method. The working procedure must be carried out as rapidly as possible in which the introduction of actinic light should be avoided.

Sample solution (a): Dissolve 0.500 g of the solution to be investigated in trimethylpentane and dilute with the same solvent to 25.0 ml.

Sample solution (b): Add 1.0 ml of a 2.5 g/l solution of p-anisidine in glacial acetic acid to 5.0 ml of sample solution (a), shake and store protected from light.

Comparative solution: Add 1.0 ml of a 2.5 g/l solution of p-anisidine in glacial acetic acid to 5.0 ml of trimethylpentane, shake and store protected from light. Measure the degree of absorption of the sample solution (a) at 350 nm maximum in which trimethylpentane is used as compensation liquid. Measure the degree of absorption of the sample solution (b) at 350 nm exactly 10 minutes after preparation in which the comparative solution is used as compensation liquid. The anisidine number (AN) is calculated from the following equation:

$$AN=(25*(1.2*A1-A2))/m$$

A1=Degree of absorption of the sample solution (b) at 350 nm,
A2=Degree of absorption of the sample solution (a) at 350 nm,
m=mass of the substance to be investigated in the sample solution (a) in grams.

If the stability of the samples to oxidation is compared, by (1) measuring the degree of oxidation, (2) subjecting the samples to oxidizing conditions and (3) measuring again the degree of oxidation, the degree of oxidation in the context of the present invention in steps (1) and (3) is preferably evaluated by determining the peroxide number (PN) and/or the anisidine number (AN); furthermore, the oxidizing conditions in step (2) are preferably selected from one of the following: Storage in open containers which have been exposed to air at room temperature over a predetermined period of time of at least ten days; storage in open containers which have been exposed to air at 50° C. over a predetermined period of time of at least three days.

It has been found, surprisingly, that the sensitivity to oxidation of the omega-3 fatty acid salts prepared according to the invention are dependent not only on the temperature set in the preparation process but also on the water content used in the preparation process.

In a preferred embodiment of the method according to the invention, the basic amines are basic amino acids, chosen from lysine, arginine, ornithine or mixtures thereof in different ratios.

It is further preferred to use L-lysine or mixtures of L-lysine and L-arginine as basic amines and that the ratio between L-lysine and L-arginine is between 10:1 and 1:1.

In a further advantageous embodiment the composition additionally comprises between 1% by weight and 10% by weight, preferably between 3% by weight and 7% by weight of an earth alkali metal salt, preferably a magnesium salt. The use of magnesium-salts is further preferred, chosen from magnesium stearate or magnesium hydroxide.

In a further preferred embodiment between 1% by weight and 10% by weight of an excipient can be added to the composition. An "excipient" is a substance formulated alongside the active ingredient, included for the purpose of long-term stabilization, bulking up solid formulations or for facilitating adsorption, reducing viscosity, enhancing solubility or being useful in the manufacturing process to aid handling of the active substance.

Preferred excipients are chosen from disintegrants: magnesium hydroxide ($Mg(OH)_2$), magnesium stearate, PUFA sodium salts, PUFA potassium salts, glycine, sodium chloride (NaCl), glycerine, or plasticisers: magnesium hydroxide (Mg(OH)2), magnesium stearate, choline, arginine, glycerine. For taste improvement glycine or glycerine can be used. Moreover, further substances with additional health benefits can be added to the composition, chosen from: monoacylglycerides, creatine or essential amino acids such as leucine, isoleucine, valine, histidine, methionine, phenylalanine and threonine.

In a preferred configuration of the method according to the invention, the dispersion used comprises 5% by weight to 10% by weight water, preferably 7% by weight to 8% by weight water, based on the total weight of the dispersion.

In a further preferred configuration of the method according to the invention, the adjusted temperature is in the range from 25° C. to 100° C., preferably in the range from 40° C. to 80° C.

In preferred aspects of the present invention, preferred starting dispersions comprise significant amounts of free fatty acids. Accordingly, the total amount of fatty acids (i.e. fatty acids with free carboxyl groups) is preferably at least x percent by weight of the starting dispersion, without taking into account the volatile constituents, where x is selected from 30, 40, 50, 60, 65.

In preferred aspects of the present invention, preferred starting dispersions comprise significant amounts of a basic amino acid. Accordingly, the total amount of the basic amino acid is preferably at least y percent by weight of the starting dispersion, without taking into account the volatile constituents, where y is selected from 15, 20, 25, 30.

Omega-3 fatty acids, which may be used individually or in any combination in the method according to the invention, comprise for example α-linolenic acid (ALA) 18:3 (n-3) (cis,cis,cis-9,12,15-octadecatrienoic acid), stearidonic acid (SDA) 18:4 (n-3) (all-cis-6,9,12,15,-octadecatetraenoic acid), eicosatrienoic acid (ETE) 20:3 (n-3) (all-cis-11,14,17-eicosatrienoic acid), eicosatetraenoic acid (ETA) 20:4 (n-3) (all-cis-8,11,14,17-eicosatetraenoic acid), heneicosapentaenoic acid (HPA) 21:5 (n-3) (all-cis-6,9,12,15,18-heneicosapentaenoic acid), docosapentaenoic acid (clupanodonic acid) (DPA) 22:5 (n-3) (all-cis-7,10,13,16,19-docosapentaenoic acid, tetracosapentaenoic acid 24:5 (n-3) (all-cis-9,12,15,18,21-tetracosapentaenoic acid), tetracosahexaenoic acid (nisinic acid) 24:6 (n-3) (all-cis-6,9,12,15,18,21-tetracosahexaenoic acid).

Polyunsaturated omega-3 fatty acids, which may be used in the method according to the invention, may be obtained from any suitable starting material, which may in addition be processed with any suitable method. Typical starting materials include all parts of fish carcasses, vegetables and other plants, and also material from microbial fermentation or fermentation of algae. Typical processing methods for such starting materials are, inter alia, steps for crude oil extraction, such as extraction and separation of the starting materials and also steps for refining crude oils, such as deposition and degumming, deacidification, bleaching and deodorant (cf. e.g. "EFSA Scientific Opinion on Fish Oil for Human Consumption"). It is advantageous to use different plant oils as starting material, such as linseed oil, algal oil, hemp seed oil, rapeseed oil, borage seed oil, flaxseed oil, canola oil, soybean oil. Further processing methods include, inter alia, steps for the at least partial conversion of omega-3 fatty acid esters to the corresponding free omega-3 fatty acids or inorganic salts thereof.

In a further preferred embodiment of the present invention the source for omega-3 fatty acids is chosen from at least one of the following: fish oil, squid oil, krill oil, linseed oil, borage seed oil, algal oil, hemp seed oil, rapeseed oil, flaxseed oil, canola oil, soybean oil Polyunsaturated omega-3 fatty acids, which may be used in the method according to the invention, may also be obtained by cleaving the omega-3 fatty acid esters and subsequent removal of the alcohols previously attached as ester from compositions which consist principally of omega-3 fatty acid esters. The ester cleavage is preferably carried out under basic conditions. Methods for ester cleavage are well known from the prior art.

In the context of the present invention, preferred omega-3 fatty acids to be used are eicosapentaenoic acid ("EPA") and docosahexaenoic acid ("DHA"). It is further preferred to use a mixture of eicosapentaenoic acid ("EPA") and docosahexaenoic acid ("DHA").

In a preferred configuration of the method according to the invention, a mixture of omega-3 fatty acids is used which comprise in total 30% by weight or more, preferably 50% by weight or more, particularly preferably 70% by weight or more, especially preferably 90% by weight or more, eicosapentaenoic acid and docosahexaenoic acid, based on the total weight of the fatty acids.

The molar ratio M of the sum total of all carboxyl groups of the fatty acids to the sum total of all basic amine molecules should be as equimolar as possible in order to enable a maximum quantitative salt formation.

In a preferred configuration of the method according to the invention, the molar ratio M of the sum total of all carboxyl groups of the fatty acids to the sum total of all basic amine molecules is in the range 0.8≤M≤1.2, more preferably in the range 0.9≤M≤1.1, even more preferably in the range 0.95≤M≤1.05, especially preferably in the range 0.98≤M≤1.02.

Surprisingly, the omega-3 fatty acid salts prepared according to the invention can be dried without difficulty.

Therefore, in a preferred configuration of the method according to the invention, the resulting composition is dried, preferably in a temperature range of 50° C. to 60° C. and at a pressure of 20 mbar or less, until a solid is obtained. The resulting solid preferably has a water content of ≤2% by weight, particularly preferably ≤1% by weight, measured by Karl-Fischer titration.

In an alternative embodiment, the composition is extruded after kneading in a continuous process to obtain a solid material.

It has also been found, surprisingly, that the omega-3 fatty acid salts prepared according to the invention are very brittle and can be readily milled with standard mills, a Retsch ball mill for example, although this was not necessarily to be expected due to the properties of the omega-3 fatty acid salts described earlier.

Therefore, in a preferred configuration of the method according to the invention, the solid obtained is milled.

A composition according to the invention comprising 90% by weight or more omega-3 fatty acid salt(s) typically has a particle size $D_{90}$ of 100 μm or more and a particle size $D_{50}$ of 17 μm or more and a particle size $D_{10}$ of 5 μm or more, when the composition has been milled for a period of 30 minutes in a Retsch ball mill type SM1 at a grinding speed of 250 revolutions per minute and a diameter of the grinding balls of 30 mm.

The present invention therefore also relates to a composition comprising 90% by weight or more omega-3 fatty acid salt(s), characterized in that the composition has a particle size $d_{90}$ of 100 μm or more, preferably 120 μm or more, particularly preferably 140 μm or more, and a particle size $d_{50}$ of 17 μm or more, preferably 19 μm or more, particularly preferably 21 μm or more, and a particle size $d_{10}$ of 5 μm or more, preferably 6 μm or more, particularly preferably 7 μm or more, when the composition has been milled for a period of 30 minutes in a Retsch ball mill type SM1 at a grinding speed of 250 revolutions per minute and a diameter of the grinding mills of 30 mm.

The present invention also relates in a further aspect to a composition obtainable or obtained by the method according to the invention described here. Accordingly, the present invention also relates to a composition obtainable or obtained by a method which is characterized in that a paste comprising one or more omega-3 fatty acid(s), one or more basic amine(s) and 20% by weight or less water, based on the total weight of the paste, at a temperature of 130° C. or less is kneaded for a period of time between 30 seconds and 60 minutes until a homogenous paste is obtained. The composition has the advantage of a high density and especially a high bulk density referring to the milled product. The bulk density of the product obtained is at least 0.3 g/ml, preferably at least 0.5 g/ml, more preferably at least 0.6 g/ml.

The present invention also relates to the use of a composition according to the invention for the preparation of foodstuffs, food supplements or pharmaceutical products.

In the context of the present invention, foodstuffs and food supplements comprise, without being limited thereto, bakery goods, vitamin additives, beverage powders, kneaded dough, batter, baked foodstuffs such as cakes, cheese cakes, pies, cupcakes, biscuits, bread, bread rolls, cookies, muffins, pastries, scones and croutons; liquid foodstuff products such as drinks, energy drinks, infant formula, liquid meals, fruit juices, multivitamin syrups, meal replacements; semi-solid foodstuff products such as baby formula, yoghurt, cheese, cereal flakes, pancake mixtures; nutrition bars such as energy bars; processed meat; ice cream; frozen desserts; frozen yoghurts; wafer mixtures; salad dressings; egg substitute mixtures; cookies, crackers, confectionery, snacks, muesli/snack bars, pop-tarts, salted nibbles such as potato crisps, corn chips, tortilla chips, extruded snacks, popcorn, and nuts; particular snacks such as dips, dried fruits, meat snacks, fried snacks, health bars and rice/corn wafers; confectionery such as sweets; instant foodstuffs such as instant noodles, instant stock cubes or instant powders.

In the context of the present invention, pharmaceutical products may comprise, in addition to the omega-3 fatty acid salts described here, both pharmaceutically acceptable auxiliaries and pharmaceutical active ingredients such as statins, anti-hypertensive agents, antidiabetics, antidementia agents, antidepressants, anti-obesity agents, appetite suppressants and agents to improve memory and/or cognitive function.

As already stated, salts of basic amino acids and polyunsaturated fatty acids are known from the prior art (cf. EP 0734373 B1), although it was not known that salts of L-lysine or other basic amines and polyunsaturated fatty acids could be prepared by kneading a paste of polyunsaturated fatty acids, L-lysine or other basic amino acids and water. It is important in this context that salts of basic amino acids and polyunsaturated fatty acids have hitherto been described as "very thick, transparent oils, which transform at low temperatures into solids having a waxy appearance and a waxy nature" (cf. EP 0734373 B1, p. 1, lines 47-48). Consequently, a person skilled in the art would not have expected that omega-3 fatty acid salts can be prepared by kneading a paste of omega-3 fatty acids, L-lysine or other basic amines and water. It was therefore surprising that in the context of the present invention it has been found that omega-3 fatty acid salts can in fact be obtained easily by kneading. As already described at the outset, the kneading conditions can be adjusted to the temperature set in each case and the amount of water used. Such adjustments are however part of the routine laboratory work of an average person skilled in the art.

The method according to the invention is described here in detail for the use with omega-3 fatty acids. The use of omega-6 fatty acids is however also possible.

Omega-6 fatty acids, which may be used individually or in any combination in the method according to the invention, comprise, for example, γ-Linolenic acid (GLA) 18:3 (n-6) (all-cis-6,9,12-octadecatrienoic acid), Linoleic acid (LA) 18:2 (n-6) ((9Z,12Z)-9,12-Octadecadienoic acid), eicosadienoic acid 20:2 (n-6) (all-cis-11,14-eicosadienoic acid), dihomogammalinolenic acid (DGLA) 20:3 (n-6) (all-cis-8,11,14-eicosatrienoic acid), arachidonic acid (ARA) 20:4 (n-6) (all-cis-5,8,11,14-eicosatetraenoic acid), docosadienoic acid 22:2 (n-6) (all-cis-13-16-docosadienoic acid), adrenic acid 22:4 (n-6) (all-cis-7,10,13,16-docosatetraenoic acid), docosapentaenoic acid (osbond acid) 22:5 (n-6) (all-cis-4,7,10,13,16-docosapentaenoic acid), tetracosatetraenoic acid 24:4 (n-6) (all-cis-9,12,15,18-tetracosatetraenoic acid), tetracosapentaenoic acid 24:5 (n-6) (all-cis-6,9,12,15,18-tetracosapentaenoic acid).

The present invention is described in detail by means of the following non-limiting experiments.

EXPERIMENTS

Analytical Methods:

Primary oxidation products (hydroperoxides at double bonds) were determined quantitatively by the determination of the peroxide number (PN) according to Ph. Eur. 2.5.5 (01/2008:20505). Secondary oxidation products (carbonyl compounds) were determined quantitatively by the determination of the anisidine number (AN) according to Ph. Eur. 2.5.36 (01/2008:20536).

Oligomeric omega-3 fatty acid constituents and derivatives thereof (referred to in summary as oligomer content) were quantified by gel chromatography (GPC, styrene-divinylbenzene phase with tetrahydrofuran containing trifluoroacetic acid as eluent). A refractive index detector (RI) was used for the determination. Since specific reaction factors for the constituents of the samples were unknown, the quantitative ratios were calculated on the basis of the refractive ratios of the total area of the chromatogram.

The water content was determined by Karl-Fischer titration.

Acid values were determined by titration with potassium hydroxide.

1. Experiment with 3.8% Water Addition 270.0 g of fatty acid (prepared from a fish oil with fatty acid contents of 50% EPA and 20% DHA) with an acid number of 178.85 mg KOH/g and 141.4 g of lysine monohydrate (this corresponds to 125.9 g of L-lysine and 15.5 g of water) were charged in the kneader (Thermo-Fisher Rheomix 3000E, volume ca. 310 ml with roller rotors (R3)) and subsequently kneaded initially at 70-90° C. Since initially a homogeneous mixture was not formed, the temperature was increased to 120° C. A homogeneous melt was formed from the outgassed water vapour in the form of bubbles. After ca. 10 min at 120° C., the mixture was discharged from the kneader. This gave 339 g of a product which solidified on cooling. 294.2 g of the moist product were dried overnight in the drying cabinet at 50-60° C. and 20 mbar. After comminuting, this gave 283 g of a solid having a bulk density of 0.665 g/ml.

2. Experiment with 7.5% Water Addition 250.0 g of fatty acid (prepared from a fish oil with fatty acid contents of 50% EPA/20% DHA) with an acid number of 178.85 mg KOH and 131.0 g of lysine monohydrate (this corresponds to 116.6 g of L-lysine and 14.4 g of water) were reacted with addition of 15.3 g of water analogously to Experiment 1 for 10 min at 50° C. This gave 376 g of moist product as a plastic solid. 335.8 g of the moist product were dried overnight in the drying cabinet at 50-60° C. and 20 mbar. After comminuting, this gave 313 g of a solid having a bulk density of 0.585 g/ml.

3. Experiment with 15% Water Addition 230.0 g of fatty acid (prepared from a fish oil with fatty acid contents of 50% EPA/20% DHA) with an acid number of 175.3 mg KOH and 117.8 g of lysine monohydrate (this corresponds to 104.9 g of L-lysine and 12.9 g of water) were reacted with addition of 46.2 g of water analogously to Experiment 1 for 60 min at 25° C. This gave 373 g of moist product as a cream. 333 g of the moist product were dried overnight in the drying cabinet at 50-60° C. and 20 mbar, whereupon a solid foam formed. After comminuting, this gave 282 g of a solid having a bulk density of 0.375 g/ml.

4. Experiment with 20.4% Water Addition 200.0 g of fatty acid (prepared from a fish oil with fatty acid contents of 50% EPA/20% DHA) with an acid number of 175.3 mg KOH and 102.5 g of lysine monohydrate (this corresponds to 91.2 g of L-lysine and 11.3 g of water) were reacted with addition of 63.5 g of water analogously to Experiment 1 for 60 min at 25° C. This gave 371 g of moist product as a sticky paste. 330 g of the moist product were dried overnight in the drying cabinet at 50-60° C. and 20 mbar, whereupon a solid foam formed. After comminuting, this gave 265 g of a solid having a bulk density of 0.347 g/ml.

5. Comparative Experiment without Addition of Water 250.0 g of fatty acid (prepared from a fish oil with fatty acid contents of 50% EPA/20% DHA) with an acid number of 175.3 mg KOH/g and 114 g of anhydrous lysine were charged in the kneader (Thermo-Fisher Rheomix 3000E, volume ca. 310 ml with roller rotors (R3)) and subsequently kneaded initially at 100° C. Since initially a homogeneous mixture was not formed, the temperature was increased stepwise to 150° C. After 20 min at 150° C., the experiment was terminated and the mixture was discharged from the kneader. This gave 330 g of a product in which very significant inclusions of solid lysine were still apparent.

The conditions of the kneading experiments in the Thermo-Fisher Rheomix 3000E and the water contents after drying at 50-60° C./20 mbar are summarized in Table 1. In the experiments, the products were scraped out of the kneader mechanically after cooling.

TABLE 1

| Experiment No. | Water content [% by weight] | Temperature [° C.] | Time [min] | Water content after drying [% by weight] | Bulk density [g/ml] |
|---|---|---|---|---|---|
| 5 | 0.0 | 150 | 20 | 0.63 | n.d. |
| 1 | 3.8 | 120 | 10 | 0.43 | 0.665 |
| 2 | 7.5 | 55 | 10 | 0.22 | 0.585 |
| 3 | 15.0 | 25 | 60 | 0.20 | 0.375 |
| 4 | 20.4 | 22 | 60 | 0.31 | 0.347 |

Whereas with 20.4% and 15.0% water, a homogeneous mixture was already obtained by kneading at room temperature, in the experiments with 7.5% and 3.8% (this corresponds to the use of lysine monohydrate), temperatures of 55° C. and 130° C. had to be applied for this. In the experiment without addition of water, no homogeneous mixture was achieved even after 20 min at 150° C. Certain amounts of solid lysine were still noticeable in the product afterwards.

Whereas the products with 0%, 3.8% and 7.5% water on drying at 50-60° C. under reduced pressure did not noticeably change their form, the products with 15% and 20.4% water formed solid foams but which could be readily comminuted. However, the foam formation leads to a distinct reduction in the bulk density of the dried comminuted solids (Table 1). Whereas those with 3.8% and 7.5% water are at 0.665 g/ml or 0.585 g/ml respectively, those with 15% and 20.4% water were obtained only with bulk densities of 0.375 g/ml or 0.347 g/ml respectively. After milling however, no significant difference was then observable. In all cases, residual water contents of below 0.5% were achieved.

The anisidine and peroxide numbers (AN) and (PN) and the oligomer contents of the products of the kneading experiments in the Thermo-Fisher Rheomix 3000E are summarized in Table 2.

TABLE 2

| Experiment No. | Water addition [% by weight] | Temperature [° C.] | AN | PN | TOTOX number (2PN + AN) | Oligomers [area %] |
|---|---|---|---|---|---|---|
| 5 | 0.0 | 150 | 7.2 | 4.0 | 15.1 | 5.3 |
| 1 | 3.8 | 120 | 26.1 | <1 | 28.1 | 0.5 |
| 2 | 7.5 | 55 | 2.6 | <1 | 4.6 | 0.2 |
| 3 | 15.0 | 25 | 3 | <1 | 5 | 0.2 |
| 4 | 20.4 | 22 | 5.1 | <1 | 7.1 | 0.2 |

As the values determined from the samples show, both the TOTOX number and the oligomer content increases with temperature. While the values for the samples with 3.8% water are still acceptable, in the sample without addition of water both the TOTOX number and the oligomer content is significantly increased.

6. Milling Experiments with the Products from Experiments 1 to 5

Ca. 70 g in each case of the dried samples from experiments 1 to 4 were milled in a Retsch ball mill type SM1 for 30 min each at a grinding speed of 250 revolutions per minute and a diameter of the grinding balls of 30 mm. The volume of the milling pot was 250 ml and both milling pot and ball mills were manufactured by Achat. The particle size distributions of the milled products are summarized in Table 3.

TABLE 3

| Experiment No. | d10 [μm] | d50 [μm] | d90 [μm] |
|---|---|---|---|
| 1 | 5.6 | 18.0 | 117.1 |
| 2 | 6.0 | 20.8 | 135.8 |
| 3 | 7.4 | 24.7 | 143.7 |
| 4 | 5.6 | 15.3 | 79.4 |

Using the standard ball mill, all products of the kneading experiment could be milled after drying to average particle sizes of below 50 μm. The product obtained from the experiment without addition of water, in which salt formation was not complete, gave thin flakes in the ball mill with diameters of ca. 5 mm which were easily bendable. A similar result can be expected for products with higher residual water contents.

7. Milling Experiment with Pinned Disc Mill

Ca. 200 g of a granulated product having an average particle size of 200 μm were milled in a Jehmlich pinned disc mill Rekord 224 at 17 000 rpm. The product could be milled to particle sizes of $d_{90}$ 13.2 μm and $d_{50}$ of 3.2 μm, without any caking being noticeable in the mill.

Different ratios of Lysine and Arginine (referring to molar %) were used for salt formation and kneading experiments were performed.

8. Experiment with Lysine-Arginine Mixture (Molar Ratio 95:5)

123.2 g of lysine monohydrate (this corresponds to 109.7 g of L-lysine and 13.5 g of water) and 6.9 g of arginine were charged in the kneader (Cooking Chef Major, model KM096, Kenwood) with addition of 27.5 g of water and subsequently kneaded initially at 50-60° C. After addition of 250.0 g of fatty acid (prepared from a fish oil with fatty acid contents of 50% EPA and 20% DHA) with an acid number of 3.2 mmol KOH/g the mixture was further kneaded at 50-60° C. with a planetary kneading hook at ~60 rpm until a homogenous paste is formed. This gave 407.6 g of a product paste which was extruded and the extruded strands were dried at 60° C. and kept under gentle nitrogen flow to retain the structure of the extrudate. The dough-like paste obtained was brittle with poor binding properties. The extrudate broke easily.

9. Experiment with Lysine-Arginine Mixture (Molar Ratio 90:10)

116.7 g of lysine monohydrate (this corresponds to 103.9 g of L-lysine and 7 g of water) and 13.8 g of arginine were reacted with 27.6 g of water and 250.0 g of fatty acid (prepared from a fish oil with fatty acid contents of 50% EPA and 20% DHA) with an acid number of 3.2 mmol KOH/g analogously to Experiment 8. This gave 408.1 g of a product paste which was extruded and the extruded strands were dried as described in Experiment 8. The dough-like paste obtained was stable and well processable with acceptable binding properties. The extrudate was stable.

10. Experiment with Lysine-Arginine Mixture (Molar Ratio 70:30)

181.6 g of lysine monohydrate (this corresponds to 161.7 g of L-lysine and 19.9 g of water) and 82.6 g of arginine were reacted with 55.8 g of water and 500.0 g of fatty acid (prepared from a fish oil with fatty acid contents of 50% EPA and 20% DHA) with an acid number of 3.2 mmol KOH/g analogously to Experiment 8. This gave 820.0 g of a product paste which was extruded and the extruded strands were dried as described in Experiment 8. The dough-like paste obtained was very well processable with excellent binding properties. The extrudate was stable.

11. Experiment with Lysine-Arginine Mixture (Molar Ratio 30:70)

77.8 g of lysine monohydrate (this corresponds to 69.3 g of L-lysine and 8.5 g of water) and 192.7 g of arginine were reacted with 38.1 g of water and 500.0 g of fatty acid (prepared from a fish oil with fatty acid contents of 50% EPA and 20% DHA) with an acid number of 3.2 mmol KOH/g analogously to Experiment 8. This gave 808.6 g of a product paste which was extruded and the extruded strands were dried as described in Experiment 8. The dough-like paste obtained was very stiff and nearly not processable with the kneader. The extrudate was sticky.

12. Experiment with Lysine-Choline Mixture (Molar Ratio 95:5)

123.2 g of lysine monohydrate (this corresponds to 109.7 g of L-lysine and 13.5 g of water) and 9.6 g of choline solution (with 50 wt-% choline, containing 4.8 g choline) were reacted with 10.0 g of water and 250.0 g of fatty acid (prepared from a fish oil with fatty acid contents of 50% EPA and 20% DHA) with an acid number of 3.2 mmol KOH/g analogously to Experiment 8. This gave 406.3 g of a product paste which was extruded and the extruded strands were dried as described in Experiment 8. The dough-like paste obtained was well processable with acceptable binding properties. The extrudate was stable.

13. Experiment with Addition of Magnesium Hydroxide 116.7 g of lysine monohydrate (this corresponds to 103.9 g of L-lysine and 7 g of water) and 4.6 g of magnesium hydroxide (corresponding to 1.9 g magnesium) were reacted with 20.0 g of water and 250.0 g of fatty acid (prepared from a fish oil with fatty acid contents of 50% EPA and 20% DHA with an acid number of 3.2 mmol KOH/g analogously to Experiment 8. This gave 398.8 g of a product paste which was extruded and the extruded strands were dried as described in Experiment 8. The dough-like paste obtained was well processable with acceptable binding properties. The extrudate was stable.

14. Experiment Using Linseed Oil and Lysine-Arginine Mixture (Molar Ratio 90:10)

133.0 g of lysine monohydrate (this corresponds to 118.4 g of L-lysine and 14.6 g of water) and 15.7 g of arginine were reacted with 28.8 g of water and 250.0 g of fatty acids (prepared from Linseed oil) with an acid number of 3.6 mmol KOH/g analogously to Experiment 8. This gave 427.5 g of a product paste which was extruded and the extruded strands were dried as described in Experiment 8. The dough-like paste obtained was stable and well processable with excellent binding properties. The extrudate was stable.

Similar results were obtained with fatty acids prepared from Linseed oil and L-lysine monohydrate. Further, kneading experiments were performed using a borage seed oil with 10 mol % magnesium hydroxide as additive and similar stable extrudates were produced. This shows that the method can be used not only with fish oil preparations but also with further non-animal PUFA sources.

The water content after drying and the density of the extruded samples as well as the anisidine and peroxide numbers (AN) and (PN) of the products of the kneading experiments in the Kenwood food processor are summarized in Table 4.

TABLE 4

| Experiment No. | Water content [% by weight] | Water content after drying [% by weight] | Density [g/ccm] | AN | PN |
|---|---|---|---|---|---|
| 8 | 7.5 | 0.66 | n.d. | 4.05 | 0.45 |
| 9 | 7.5 | 1.40 | 0.91 | 2.60 | 0.30 |
| 10 | 7.5 | 0.20 | n.d. | 1.95 | 0.34 |
| 11 | 5.0 | 0.58 | n.d. | 1.95 | 0.96 |
| 12 | 10.0 | 0.23 | 0.94 | 1.80 | 3.05 |
| 13 | 20.0 | 0.45 | 0.97 | 1.20 | 0.40 |
| 14 | 7.5 | 0.32 | 0.97 | 0.60 | 0.93 |

The density of the extruded samples ranged from 0.91 to 0.97 g/ccm. Since the products were not milled after extrusion, the density of the extruded strands was measured and was higher than 0.90 g/ccm in all experiments. The nozzle diameter for the extrusion was 3.2 mm and the diameter of the extruded strands was 3.3 mm.

It could be shown that L-lysine and L-ornithine reacted with EPA to fatty acid salts. Further, EPA/DHA mixtures were also tested with L-arginine and with L-ornithine, where fatty acid salt formation was observed. Additionally, several omega-6 fatty acids were tested (arachidonic acid, γ-Linolenic acid, Linolenic acid, Linoleic acid) and lead to salt formation with L-lysine and L-arginine. All these experiments were performed in ethanol-water mixtures and in all experiments a solid was obtained. Since fatty acid salt formation was achieved in all these experiments, it is expected that these mixtures can also be processed in a method according to the present invention using kneading.

The invention claimed is:

1. A method for preparing a composition comprising an omega-3 fatty acid salt, the method comprising:
    mixing an omega-3 fatty acid, a basic amine, and water to form a paste, wherein the paste comprises 20% by weight or less water based on a total weight of the paste; and
    kneading the paste at a temperature of 130° C. or less for a period of time between 30 seconds and 60 minutes until a homogenous paste is obtained.

2. The method according to claim 1, wherein the basic amine is at least one selected from the group consisting of lysine, arginine, ornithine, and choline.

3. The method according to claim 1, wherein the basic amine is:
    L-lysine or
    a mixture of L-lysine and L-arginine, having a ratio between the L-lysine and the L-arginine of between 10:1 and 1:1.

4. The method according to claim 1, wherein a source for the omega-3 fatty acid is at least one select from the group consisting of fish oil, squid oil, krill oil, linseed oil, borage seed oil, algal oil, hemp seed oil, rapeseed oil, flaxseed oil, canola oil, and soybean oil.

5. The method according to claim 1, wherein the composition further comprises between 1% by weight and 10% by weight of an earth alkali metal salt which is magnesium stearate, magnesium hydroxide, or a mixture thereof.

6. The method according to claim 1, wherein the composition further comprises between 1% by weight and 10% by weight of an excipient selected from the group consisting of: glycine, magnesium hydroxide, magnesium stearate, a polyunsaturated fatty acid (PUFA) sodium salt, a PUFA potassium salt, sodium chloride, a monoacylglyceride, choline, arginine, glycerine, creatine, and an essential amino acid selected from the group consisting of leucine, isoleucine, valine, histidine, methionine, phenylalanine and threonine.

7. The method according to claim 1, wherein the paste comprises 5% by weight to 10% by weight water, based on the total weight of the paste.

8. The method according to claim 1, wherein the temperature is in the range from 25° C. to 100° C.

9. The method according to claim 1, wherein the omega-3 fatty acid comprises in total 30% by weight or more eicosapentaenoic acid and/or docosahexaenoic acid, based on the total weight of the omega-3 fatty acid.

10. The method according to claim 1, wherein a molar ratio M of the sum total of all carboxyl groups of the omega-3 fatty acid to the sum total of all basic amine molecules is in a range $0.8 \leq M \leq 1.2$.

11. The method according to claim 1, wherein the composition is dried until a solid is obtained.

12. The method according to claim 1, wherein the composition is extruded after the kneading in a continuous process to obtain a solid material.

13. The method according to claim 11, wherein the solid has a water content of ≤2% by weight measured by Karl-Fischer titration.

14. The method according to claim 11, wherein the solid is milled.

15. The method according to claim 1, wherein the paste is devoid of organic solvent.

16. The method according to claim 1, wherein the method is preparing a foodstuff, a food supplement or a pharmaceutical product.

* * * * *